US009238602B1

(12) United States Patent
Stavinoha, Jr. et al.

(10) Patent No.: US 9,238,602 B1
(45) Date of Patent: *Jan. 19, 2016

(54) PROCESS FOR THE PREPARATION OF CIS-2,2,4,4-TETRAMETHYLCYCLOBUTANE-1,3-DIOL

(71) Applicant: Eastman Chemical Company, Kingsport, TN (US)

(72) Inventors: Jerome Leonard Stavinoha, Jr., Longview, TX (US); Carey Dan Ashcroft, Longview, TX (US); Kelmara Khadene Kelly, Kingsport, TN (US); Craig Alan Hoyme, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/566,154

(22) Filed: Dec. 10, 2014

(51) Int. Cl.
*C07C 29/132* (2006.01)
*C07C 29/145* (2006.01)
*C07C 29/56* (2006.01)

(52) U.S. Cl.
CPC ............. *C07C 29/132* (2013.01); *C07C 29/145* (2013.01); *C07C 29/56* (2013.01); *C07C 2101/04* (2013.01)

(58) Field of Classification Search
CPC ................................ C07C 29/145; C07C 29/56
See application file for complete search history.

(56) References Cited

U.S. PATENT DOCUMENTS

| 2,936,324 | A | * | 5/1960 | Hasek et al. | .................. | 568/839 |
| 3,000,906 | A | | 9/1961 | Hasek et al. | | |
| 3,190,928 | A | * | 6/1965 | Elam et al. | .................... | 568/839 |
| 5,169,994 | A | | 12/1992 | Sumner, Jr. et al. | | |
| 5,258,556 | A | | 11/1993 | Sumner, Jr. et al. | | |
| 7,115,239 | B2 | | 10/2006 | Forni et al. | | |
| 7,838,707 | B2 | * | 11/2010 | McCusker-Orth et al. | ... | 568/839 |
| 8,394,997 | B2 | * | 3/2013 | Liu et al. | ........................ | 568/839 |
| 8,420,868 | B2 | * | 4/2013 | Liu et al. | ........................ | 568/839 |
| 8,420,869 | B2 | * | 4/2013 | Zhu et al. | ...................... | 568/839 |
| 2003/0039604 | A1 | | 2/2003 | Niu et al. | | |
| 2006/0142148 | A1 | | 6/2006 | Ma et al. | | |
| 2006/0142149 | A1 | | 6/2006 | Ma et al. | | |
| 2006/0239893 | A1 | | 10/2006 | Zhang et al. | | |
| 2008/0175787 | A1 | | 7/2008 | Ma et al. | | |
| 2008/0176069 | A1 | | 7/2008 | Ma et al. | | |
| 2009/0208391 | A1 | | 8/2009 | Ma et al. | | |

OTHER PUBLICATIONS

Rossetti, Illenia et al., "Graphitised carbon as support for Ru/C ammonia synthesis catalyst"; Catalysis Today 102-103, (2005), pp. 219-224.
Co-pending U.S. Appl. No. 14/566,245, filed Dec. 10, 2014.
USPTO Office Action dated May 6, 2015 for co-pending U.S. Appl. No. 14/566,245.

* cited by examiner

*Primary Examiner* — Brian J Davis
(74) *Attorney, Agent, or Firm* — Betty J. Boshears; Robert C. Morriss

(57) ABSTRACT

This invention is generally directed to a process for the preparation of cis-2,2,4,4-tetramethylcyclobutane-1,3-diol comprising:

treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent in which the resulting cis-2,2,4,4-tetramethylcyclobutane-1,3-diol is partially soluble and further in the presence of a catalyst comprising about 0.1 to about 10 weight percent ruthenium, based on the total weight of the catalyst, deposited on a support material, under reaction conditions sufficient to produce a cis-2,2,4,4-tetramethylcyclobutane-1,3-diol having a final cis:trans molar ratio of from 2:1 to about 25:1.

16 Claims, No Drawings

PROCESS FOR THE PREPARATION OF CIS-2,2,4,4-TETRAMETHYLCYCLOBUTANE-1,3-DIOL

FIELD OF THE INVENTION

The invention is generally directed to a process for preparing high cis-2,2,4,4-tetramethylcyclobutane-1,3-diol by operating under conditions such that cis-2,2,4,4-tetramethylcyclobutane-1,3-diol is partially soluble in the reaction solvent.

BACKGROUND OF THE INVENTION

The monomer, 2,2,4,4-tetramethylcyclobutane-1,3-diol, (TMCD) is an important intermediate for producing a variety of polymeric materials which possess advantageous properties. For example, polyesters derived from dicarboxylic acids and 2,2,4,4-tetramethylcyclobutane-1,3-diol can possess higher glass transition temperatures, impact strength, weatherability, and hydrolytic stability in comparison to many other polyesters prepared from other commonly-used diols. TMCD (II) can be prepared by the catalytic hydrogenation of 2,2,4,4-tetramethylcyclobutane-1,3-dione (I), as illustrated in following schematic:

Hydrogenation of
2,2,4,4-Tetramethylcyclobutane-1,3-dione

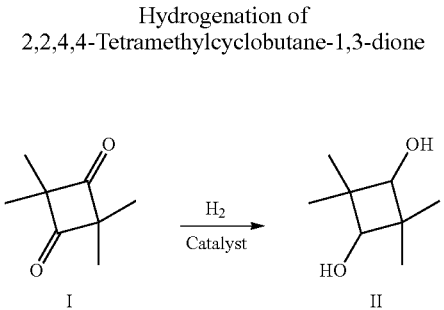

The hydrogenation of 2,2,4,4-tetramethylcyclobutane-1,3-dione produces 2,2,4,4-tetramethylcyclobutane-1,3-diol as a mixture of cis and trans isomers. For example, U.S. Pat. No. 3,190,928 discloses the hydrogenation of 2,2,4,4-tetramethylcyclobutane-1,3-dione using nickel- or ruthenium-based catalysts to produce 2,2,4,4-tetramethylcyclobutane-1,3-diol with molar cis:trans ratios that can vary widely from about 0.5 to about 1.2. The cis:trans ratio is typically about 1:1 to 1.5:1 in most solvents. The cis:trans ratio is even lower when a nickel catalyst is used for the hydrogenation. The only methods believed to be known in the art to obtain primarily cis-2,2,4,4-tetramethylcyclobutane-1,3-diol involve physical separation of the cis isomer from trans isomer. In order to obtain high overall conversion to cis-2,2,4,4-tetramethylcyclobutane-1,3-diol in these physical separation processes, the recovered trans-2,2,4,4-tetramethylcyclobutane-1,3-diol must be isomerized again to a mixture of cis and trans isomers, thus requiring even more processing and a large recycle loop.

Also, catalysts that produce the most desirable ratio of cis:trans isomers may not give the best yields or highest rates of hydrogenation. The cis:trans isomer ratio of 2,2,4,4-tetramethylcyclobutane-1,3-diols can influence important properties such as, for example, the glass transition temperature, impact strength, and crystallization rate of the polyester polymers prepared from them. A cis:trans ratio that varies widely, in turn, can give polyesters with inconsistent and/or undesirable properties. A process that produces high cis:trans ratios, therefore, would be desirable in order to produce 2,2,4,4-tetramethylcyclobutane-1,3-diol with consistently high cis:trans ratios regardless of the hydrogenation catalyst used. Such a process also would enable the efficient production of polyesters from 2,2,4,4-tetramethlycyclobutane-1,3-diol with properties that can be tailored to a variety of applications.

SUMMARY OF THE INVENTION

This invention is believed to meet the above described need in the art. This process provides for the direct preparation of cis-2,2,4,4-tetramethylcyclobutane-1,3-diol.

It has been found that the cis:trans ratio of 2,2,4,4-tetramethylcyclobutane-1,3-diol may be substantially modified by contacting either 2,2,4,4-tetramethylcyclobutane-1,3-dione, and/or 3-hydroxy-2,2,4,4-tetramethylcyclobutanone, and/or a mixture of cis and trans 2,2,4,4-tetramethylcyclobutane-1,3-diol with hydrogen and a ruthenium catalyst. The cis:trans ratio may be substantially increased by operating under conditions such that cis-2,2,4,4-tetramethylcyclobutane-1,3-diol is partially soluble in the reaction solvent.

A general embodiment of our invention, therefore, is a process for the preparation of a 2,2,4,4-tetramethylcyclobutane-1,3-diol, comprising contacting either 2,2,4,4-tetramethylcyclobutane-1,3-dione, and/or 3-hydroxy-2,2,4,4-tetramethylcyclobutanone, and/or 2,2,4,4-tetramethylcyclobutane-1,3-diol having a molar ratio of cis to trans isomers of 0:1 to about 2:1, with hydrogen in the presence of a catalyst comprising about 0.1 to about 10 weight percent ruthenium, based on the total weight of the catalyst, deposited on a support material, to produce a 2,2,4,4-tetramethylcyclobutane-1,3-diol having a molar ratio of cis to trans isomers from about 2:1 to about 25:1 or from about 3:1 to about 25:1. The process of the invention involves the use of a reaction solvent in which cis-2,2,4,4-tetramethylcyclobutane-1,3-diol is partially soluble.

In one embodiment of the invention, there is provided a process for the preparation of cis-2,2,4,4-tetramethylcyclobutane-1,3-diol comprising treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent in which the resulting cis-2,2,4,4-tetramethylcyclobutane-1,3-diol is partially soluble, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1.

In one embodiment, the process of the invention includes a process for the separation of cis-2,2,4,4-tetramethylcyclobutane-1,3-diol comprising treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from water, at least one hydrocarbon, or mixtures thereof, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1

In one embodiment, the process of the invention comprises a process for the preparation of cis-2,2,4,4-tetramethylcyclobutane-1,3-diol comprising treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from at least one hydrocarbon, at least one secondary alcohol, or mixtures thereof, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1.

The process of the invention may be used for the preparation of 2,2,4,4-tetramethylcyclobutane-1,3-diol in a cis:trans ratio greater than about 2:1 to about 25:1 or from about 3:1 to about 25:1 by reacting 2,2,4,4-tetramethylcyclobutane-1,3-dione with hydrogen in the presence of a catalyst comprising about 0.1 to about 10 weight percent ruthenium, based on the total weight of the catalyst, deposited on a support comprising silica, alumina, silica-alumina, titania, zirconia, activated carbon, graphitized carbon, carbon nanotubes, zeolites, chromia, rare earth metal oxides, or mixtures thereof at a pressure of about 0.4 to about 7 megapascals and a temperature of about 60 to about 130° C. with a solvent in which 2,2,4,4-tetramethylcyclobutane-1,3-diol is partially soluble under the reaction conditions.

Another embodiment of our invention is a process for the preparation of cis-2,2,4,4-tetramethylcyclobutane-1,3-diol, comprising contacting 2,2,4,4-tetramethylcyclobutane-1,3-diol having a molar ratio of cis to trans isomers of 0:1 to about 2:1 with hydrogen in the presence of a catalyst comprising about 0.1 to about 10 weight percent ruthenium, based on the total weight of the catalyst, deposited on a support at a pressure of about 0.4 to about 7 megapascals and a temperature of about 60 to about 130° C. with a solvent in which cis-2,2,4,4-tetramethylcyclobutane-1,3-diol is partially soluble under the reaction conditions to produce an isomerized 2,2,4,4-tetramethylcyclobutane-1,3-diol having a molar ratio of cis to trans isomers of from about 2:1 to about 25:1 or from about 3:1 to about 25:1.

In one embodiment, there is a provided a process for the isomerization of a 2,2,4,4-tetramethylcyclobutane-1,3-diol, comprising contacting trans-2,2,4,4-tetramethylcyclobutane-1,3-diol with a catalyst comprising about 1 to about 9 weight percent ruthenium, based on the total weight of the catalyst, deposited on a support comprising silica, alumina, silica-alumina, titania, zirconia, activated carbon, carbon nanotubes, graphitized carbon, zeolites, chromia, rare earth metal oxides, or mixtures thereof at a pressure of about 0.4 to about 3.5 megapascals and a temperature of about 60 to 130° C. to form cis-2,2,4,4-tetramethylcyclobutane-1,3-diol, wherein the process has no net production of 2,2,4,4-tetramethylcyclobutane-1,3-diol.

In one embodiment, the process of the invention comprises reaction conditions which comprise a reaction temperature of about 50 to about 150° C. and a hydrogen pressure of about 0.4 to about 10 megapascals.

The process of the invention wherein said reaction conditions comprise a reaction temperature of about 70 to about 130° C. and a hydrogen pressure of about 0.4 to about 5.0 megapascals.

In one embodiment, the catalyst useful in the invention comprises about 1 to about 9 weight percent ruthenium and the support comprises activated carbon, carbon nanotubes, graphitized carbon, silica, alumina, titania, zirconia, or a mixture thereof.

In one embodiment, the catalyst useful in the invention, in addition to ruthenium, further comprises at least one metal selected from nickel, copper, cobalt, rhenium, platinum, palladium, rhodium, gold, silver, chromium, manganese, tin, or mixtures thereof.

In the process of the invention, the thermodynamic cis/trans 2,2,4,4-tetramethylcyclobutane-1,3-diol ratio produced by the reaction can be greater than the cis/trans 2,2,4,4-tetramethylcyclobutane-1,3-diol solubility ratio in the reaction solvent(s) and wherein the cis-2,2,4,4-tetramethylcyclobutane-1,3-diol isomer concentration can be greater than the cis-2,2,4,4-tetramethylcyclobutane-1,3-diol solubility at the reaction temperature.

In the process of the invention, the thermodynamic cis/trans 2,2,4,4-tetramethylcyclobutane-1,3-diol ratio produced by the reaction is greater than the cis/trans 2,2,4,4-tetramethylcyclobutane-1,3-diol solubility ratio in the reaction solvent(s) and wherein the cis-2,2,4,4-tetramethylcyclobutane-1,3-diol isomer concentration is greater than the cis-2,2,4,4-tetramethylcyclobutane-1,3-diol solubility at the reaction temperature.

In one embodiment, the reaction solvent(s) are selected from water, alcohols, ethers, glycols, glycol ethers, alkanes, esters, or mixtures thereof.

In one embodiment, at least one reaction solvent can be selected from water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, branched alkanes, isoalkanes, isopropyl alcohol, methyl isobutyl carbinol, isobutyl acetate, methyl butyrate, or mixtures thereof.

Typical solvents include water, alcohols, esters, ethers, and hydrocarbons. Aldehydes and ketones, which can be converted to alcohols under the hydrogenation conditions, may be employed. For example, acetone may be converted to isopropyl alcohol under the reaction conditions. A solvent system comprising two immiscible materials, such as water and a hydrocarbon may also be employed. Solvents of two or more miscible components may also be used as long as cis-2,2,4,4-tetramethylcyclobutane-1,3-diol is partially soluble in the solvent system.

In one embodiment, the reaction solvent can be selected from at least one alkane, water, or mixtures thereof.

In one embodiment, the reaction solvent can be selected from at least one alkane.

In one embodiment, the alkane can be an isoalkane, a branched alkane, or a cyclic alkane or mixtures thereof.

In one embodiment, the branched alkane can comprise from 6 to 18 carbon atoms.

In one embodiment, the reaction solvent is water.

In one embodiment, the reaction solvent can be a mixture of water and at least one alkane.

In one embodiment, the process of the invention is conducted in the liquid phase.

In addition to the process described herein, additional steps may be used to separate and recover the catalyst and, optionally, reuse it in a subsequent process. These steps are described in the following order of sequence: removal of the reaction solvent, whether by filtration, centrifugation, or other methods known to one of ordinary skill in the art; optionally washing the solids and catalyst to remove impurities and residual solvent, dissolution of the 2,2,4,4-tetramethylcyclobutane-1,3-diol with at least one solvent and, optionally, washing the catalyst at least once, and, optionally, reuse of the catalyst.

In one embodiment of the invention, in addition to the process described above, there is provided a process for the preparation of cis-2,2,4,4-tetramethylcyclobutane-1,3-diol comprising step (A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent in which the resulting cis-2,2,4,4-tetramethylcyclobutane-1,3-diol is partially soluble and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1, and optionally the following steps:

(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally,
(D) washing the catalyst at least once, and optionally,
(E) reuse of the catalyst.

In each of the embodiments of the invention, where step (A) is present, steps (B)-(E) can also be present. In addition, in each of the embodiments of the invention where step (A) is present, it is optional prior to step (C), to wash the 2,2,4,4-tetramethylcyclobutane-1,3-diol solids and/or the catalyst.

In one embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from (i) water, at least one hydrocarbon, or mixtures thereof or (ii) at least one hydrocarbon, at least one secondary alcohol, or mixtures thereof, in which the resulting cis-2,2,4,4-tetramethylcyclobutane-1,3-diol is partially soluble and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1.

In one embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from water, at least one hydrocarbon, or mixtures thereof, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1.

In another embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from at least one hydrocarbon, at least one secondary alcohol, or mixtures thereof, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1.

In one embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent in which the resulting cis-2,2,4,4-tetramethylcyclobutane-1,3-diol is partially soluble and further in the presence of at least one catalyst comprising about 0.1 to about 10 weight percent ruthenium and at least one metal selected from, nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1.

In one embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from (i) water, at least one hydrocarbon, or mixtures thereof or (ii) at least one hydrocarbon, at least one secondary alcohol, or mixtures thereof, in which the resulting cis-2,2,4,4-tetramethylcyclobutane-1,3-diol is partially soluble and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from 2:1 to about 25:1 or from 3:1 to about 25:1t.

In one embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from water, at least one hydrocarbon, or mixtures thereof, and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1.

In another embodiment of the invention, there is provided a process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from at least one hydrocarbon, at least one secondary alcohol, or mixtures thereof, and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from 3.1 to about 25:1.

In yet another embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from (i) water, at least one hydrocarbon, or mixtures thereof or (ii) at least one hydrocarbon, at least one secondary alcohol, or mixtures thereof, in which the resulting cis-2,2,4,4-tetramethylcyclobutane-1,3-diol is partially soluble and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1;
(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally,
(D) washing the catalyst at least once, and optionally,
(E) reuse of the catalyst.

In one embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent in which the resulting cis-2,2,4,4-tetramethylcyclobutane-1,3-diol is partially soluble and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1;
(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally,
(D) washing the catalyst at least once, and optionally,
(E) reuse of the catalyst.

In one embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from (i) water, at least one hydrocarbon, or mixtures thereof or (ii) at least one hydrocarbon, at least one secondary alcohol, or mixtures thereof, in which the resulting cis-2,2,4,4-tetramethylcyclobutane-1,3-diol is partially soluble and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from 2:1 to about 25:1 or from 3:1 to about 25:1;
(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally, (D) washing the catalyst at least once, and optionally,
(E) reuse of the catalyst.

In one embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from water, at least one hydrocarbon, or mixtures thereof, and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1;
(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally,
(D) washing the catalyst at least once, and optionally,
(E) reuse of the catalyst.

In another embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from at least one hydrocarbon, at least one secondary alcohol, or mixtures thereof, and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from 3.1 to about 25:1;
(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally,
(D) washing the catalyst at least once, and optionally,
(E) reuse of the catalyst.

In yet another embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from (i) water, at least one hydrocarbon, or mixtures thereof or (ii) at least one hydrocarbon, at least one secondary alcohol, or mixtures thereof, in which the resulting cis-2,2,4,4-tetramethylcyclobutane-1,3-diol is partially soluble and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1;
(B) removal of the reaction solvent, whether by filtration, centrifugation, or other methods known to one of ordinary skill in the art;
(C) dissolution of the 2,2,4,4-tetramethylcyclobutane-1,3-diol with at least one solvent; and, optionally,
(D) washing the catalyst at least once, and optionally,
(E) reuse of the catalyst.

In yet another embodiment of the invention, there is provided a batch process for the preparation of cis-2,2,4,4-tetramethylcyclobutane-1,3-diol comprising:
(A) treatment of at least one monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol said diol having a starting cis:trans molar ratio of 0:1 to about 2:1, or mixtures thereof by contacting said monomer(s) with hydrogen in the presence of a reaction solvent selected from (i) water, at least one hydrocarbon, or mixtures thereof or (ii) at least one hydrocarbon, at least one secondary alcohol, or mixtures thereof, in which the resulting cis-2,2,4,4-tetramethylcyclobutane-1,3-diol is partially soluble and further in the presence of at least one catalyst comprising about 0.1 to about 10 weight percent ruthenium and at least one metal selected from nickel, copper, cobalt, rhenium, platinum, palladium, rhodium, gold, silver, chromium, manganese, tin, or mixtures thereof, based on the total weight of the catalyst, deposited on a support material, under reaction conditions sufficient to produce a 2,2,4,4-tetramethylcyclobutane-1,3-diol having a final cis:trans molar ratio of from about 2:1 to about 25:1 or from about 3:1 to about 25:1;
(B) removal of the reaction solvent, whether by filtration, centrifugation, or other methods known to one of ordinary skill in the art;
(C) optionally, washing the 2,2,4,4-tetramethylcyclobutane-1,3-diol solids and/or the catalyst,
(D) dissolution of the 2,2,4,4-tetramethylcyclobutane-1,3-diol with at least one solvent; and, optionally,
(E) washing the catalyst at least once, and optionally,
(F) reuse of the catalyst.

In one embodiment, the process of the invention is a single step process.

In one embodiment, the solvent system can be comprised of either a mixture of hydrocarbon and water or a mixture of hydrocarbon and alcohol.

In one embodiment, prior to step (C) of certain embodiments of the process of the invention, the cis-2,2,4,4-tetramethylcyclobutane-1,3-diol solids and/or the catalyst can optionally be washed.

In one embodiment, there is no need to physically separate the isomers.

In one embodiment, there is no need to recycle the trans isomer.

In one embodiment, there is no need to physically separate the isomers and there is no need to recycle the trans isomer.

In one embodiment, the catalyst can be re-used in a subsequent process.

In yet another embodiment, there is no need to physically separate the isomers, there is no need to recycle the trans isomer, and the catalyst can be re-used.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present disclosure may be understood more readily by reference to the following detailed description of certain embodiments of the invention and the working examples.

In accordance with the purposes of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example, 1, 2, 3, 4, etc., as well as the endpoints 0 and 10. Also, a range associated with chemical substituent groups such as, for example, "$C_1$ to $C_{10}$ hydrocarbons," is intended to specifically include and disclose $C_1$ and $C_{10}$ hydrocarbons as well as $C_2$, $C_3$, $C_4$, $C_5$, $C_6$, $C_7$, $C_8$, and $C_9$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the singular forms "a," "an," and "the" include their plural referents unless the context clearly dictates otherwise. For example, reference to the processing or making of a "bottle" or a "polyester," is intended to include the processing or making of a plurality of bottles, or polyesters. References to a composition containing or including "an" alkyl radical or "a" blend is intended to include other ingredients or other components, respectively, in addition to the one named.

By "comprising" or "containing" or "including," this disclosure intends that at least the named compound, element, particle, or method step, etc., is present in the composition or article or method, but does not exclude the presence of other compounds, catalysts, materials, particles, method steps, etc., even if the other such compounds, materials, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and it is to be understood that the recited lettering can be arranged in any sequence, unless otherwise indicated.

It has been found that the cis/trans ratio of 2,2,4,4-tetramethylcyclobutane-1,3-diol may be substantially modified by contacting either 2,2,4,4-tetramethylcyclobutane-1,3-dione and/or 3-hydroxy-2,2,4,4-tetramethylcyclobutanone and/or a mixture of cis and trans 2,2,4,4-tetramethylcyclobutane-1,3-diol with a catalyst, preferably a ruthenium catalyst, in presence of hydrogen.

A general embodiment of the invention, therefore, is a process for the preparation of a 2,2,4,4-tetramethylcyclobutane-1,3-diol, comprising contacting either 2,2,4,4-tetramethylcyclobutane-1,3-dione, and/or 3-hydroxy-2,2,4,4-tetramethylcyclobutanone, and/or 2,2,4,4-tetramethylcyclobutane-1,3-diol having a molar ratio of cis to trans isomers of 0:1 to about 2:1, with hydrogen in the presence of a catalyst comprising about 0.1 to about 10 weight percent of a catalyst, preferably ruthenium, based on the total weight of the catalyst, deposited on a support material, to produce a 2,2,4,4-tetramethylcyclobutane-1,3-diol having a molar ratio of cis to trans isomers that is from about 2:1 to about 25:1 or from about 3:1 to about 25:1.

A key component of the invention involves the use of a reaction solvent in which cis-2,2,4,4-tetramethylcyclobutane-1,3-diol is partially soluble. Typical solvents include water, alcohols, esters, ethers, hydrocarbons, and mixtures thereof. Aldehydes and ketones, which can be converted to alcohols under the hydrogenation conditions, may be employed. For example, acetone may be converted to isopropyl alcohol under the reaction conditions. A solvent system comprising two immiscible materials, such as water and a hydrocarbon may also be employed. Solvents of two or more miscible components may also be used as long as cis-2,2,4,4-tetramethylcyclobutane-1,3-diol is partially soluble in the solvent system.

The process of the invention may be used for the preparation of 2,2,4,4-tetramethylcyclobutane-1,3-diol in a cis/trans ratio greater than about 2:1 to about 25:1 or from about 3:1 to about 25:1 by reacting 2,2,4,4-tetramethylcyclobutane-1,3-dione, and/or 3-hydroxy-2,2,4,4-tetramethylcyclobutanone with hydrogen in the presence of a catalyst comprising about 0.1 to about 10 weight percent ruthenium, based on the total weight of the catalyst, deposited on a support comprising silica, alumina, silica-alumina, titania, zirconia, activated carbon, graphitized carbon, carbon nanotubes, zeolites, chromia, rare earth metal oxides, or mixtures thereof at a pressure of about 0.4 to about 7 megapascals and a temperature of about 60 to about 130° C. with a solvent in which cis-2,2,4,4-tetramethylcyclobutane-1,3-diol is only partially soluble under the reaction conditions. After the reaction step is complete, the solvent can be removed by filtration. Methanol or other suitable solvent or solvent mixtures can be added to the 2,2,4,4-tetramethylcyclobutane-1,3-diol/catalyst mixture to dissolve 2,2,4,4-tetramethylcyclobutane-1,3-diol. The solution of 2,2,4,4-tetramethylcyclobutane-1,3-diol can be then removed from the catalyst by filtration. The catalyst can be washed with methanol or other suitable solvent or solvent mixtures to remove residual 2,2,4,4-tetramethylcyclobutane-1,3-diol and then washed with a hydrocarbon to remove methanol or solvent or solvents. The catalyst may then be used in another cycle to prepare 2,2,4,4-tetramethylcyclobutane-1,3-diol in a cis/trans ratio that is greater than 2:1.

DETAILED DESCRIPTION

The process of the invention can involve the preparation and recovery of cis-2,2,4,4-tetramethylcyclobutane-1,3-diol. The recovery can be efficiently accomplished though a process. The process may then be repeated using recovered catalyst. The cis-2,2,4,4-tetramethylcyclobutane-1,3-diol may be prepared with various solvent(s) or solvent mixtures In one embodiment of the invention, the process of the invention comprises operation in a solvent comprising a hydrocarbon and water. In another embodiment of the invention, the process of the invention comprises operation in a solvent comprising a hydrocarbon and an alcohol. Thus, the hydrogenation of 2,2,4,4-tetramethylcyclobutane-1,3-dione, 3-hydroxy-2,2,4,4-tetramethylcyclobutanone, and/or isomerization of 2,2,4,4-tetramethylcyclobutane-1,3-diol to predominantly cis-2,2,4,4-tetramethylcyclobutane-1,3-diol can be conducted with a solvent that the cis-2,2,4,4-tetramethylcyclobutane-1,3-diol is partially soluble in. After the chemical transformation, the product consisting of predominantly cis-2,2,4,4-tetramethylcyclobutane-1,3-diol can be recovered by first filtration of the reaction solvent for reuse followed by dissolution of the cis-2,2,4,4-tetramethylcyclobutane-1,3-diol. After recovery of the solvent containing cis-2,2,4,4-tetramethylcyclobutane-1,3-diol, the catalyst can be washed for reuse. Since 2,2,4,4-tetramethylcyclobutane-1,3-dione first undergoes hydrogenation to 3-hydroxy-2,2,4,4-tetramethylcyclobutanone and then 3-hydroxy-2,2,4,4-tetramethylcyclobutanone undergoes hydrogenation to a mixture of cis and trans 2,2,4,4-tetramethylcyclobutane-1,3-diol, it is to be understood that any combination of these materials may be employed in this process. Any of these may be converted to 2,2,4,4-tetramethylcyclobutane-1,3-diol having a cis to trans isomer ratio of about 2:1 to 25:1. The starting 2,2,4,4-tetramethylcyclobutane-1,3-diol may have a molar ratio of cis to trans isomers of 0:1 to about 2:1. The process is conducted such that cis-2,2,4,4-tetramethylcyclobutane-1,3-diol is partially soluble under the reaction conditions. The reaction mixtures are contacted with hydrogen at a pressure of up to about 1000 psig (6.9 MPa) in the presence of a catalyst comprising about 0.1 to about 10 weight percent ruthenium, based on the total weight of the catalyst, deposited on a support. In one embodiment, the pressures can be from 100 to 700 psig (0.69 to 4.83 MPa) or 200 to 600 psig (1.38 to 4.14 MPa) or 400 to 600 psig (2.76 to 4.14 MPa) or 250 to 450 psig (1.72 to 3.10 MPa). In some embodiments, the pressures may depend on the solvent system used.

The starting 2,2,4,4-tetramethylcyclobutane-1,3-diol is typically produced by hydrogenation of 2,2,4,4-tetramethylcyclobutane-1,3-dione. A variety of metal catalysts may be used such as, for example, those catalysts containing ruthenium, nickel, copper, cobalt, rhenium, platinum, palladium, rhodium, gold, silver, chromium, manganese, tin, or mixtures thereof. For example, the hydrogenation of 2,2,4,4-tetramethylcyclobutane-1,3-dione to 2,2,4,4-tetramethylcyclobutane-1,3-diol can be carried out using nickel- or ruthenium-containing catalysts as described in U.S. Pat. Nos. 3,000,906; 3,190,928; 5,169,994; 5,258,556; and 2,936,324. Cobalt-containing catalysts also may be used. For example, U.S. Pat. Nos. 5,528,556 and 5,169,994 disclose the use of Raney cobalt for hydrogenation of 2,2,4,4-tetramethylcyclobutane-1,3-dione to 2,2,4,4-tetramethylcyclobutane-1,3-diol.

Thus, in the first mode, the process of the invention can be operated such that the hydrogenation process used to prepare 2,2,4,4-tetramethylcyclobutane-1,3-diol and the isomerization process of the trans-2,2,4,4-tetramethylcyclobutane-1,3-diol to the cis-2,2,4,4-tetramethylcyclobutane-1,3-diol occur with the same catalyst and under the same reaction conditions. The second mode allows the process to be operated independently of or in conjunction with the hydrogenation processes that are commonly used to prepare 2,2,4,4-tetramethylcyclobutane-1,3-diol from 2,2,4,4-tetramethylcyclobutane-1,3-dione. For example, another catalyst, such as nickel, could be used to prepare a mixture of cis and trans 2,2,4,4-tetramethylcyclobutane-1,3-diol. The reaction product can then be subjected to the conditions described in this invention to prepare cis-2,2,4,4-tetramethylcyclobutane-1,3-diol. Thus, the process of the invention enables the production of 2,2,4,4-tetramethylcyclobutane-1,3-diol at high cis/trans ratios regardless of the method of production of the starting 2,2,4,4-tetramethylcyclobutane-1,3-diol.

In either mode the starting 2,2,4,4-tetramethylcyclobutane-1,3-dione, 3-hydroxy-2,2,4,4-tetramethylcyclobutanone or 2,2,4,4-tetramethylcyclobutane-1,3-diol can be added to the process reactor either as a solid, in the melt phase, or in the reaction solvent or solvents. For example, 2,2,4,4-tetramethylcyclobutane-1,3-dione can be dissolved in a hydrocarbon solvent prior to being added to the reactor.

The starting 2,2,4,4-tetramethylcyclobutane-1,3-diol can be a mixture of cis and trans isomers or purified trans isomer. In one embodiment of our invention, the starting 2,2,4,4-tetramethylcyclobutane-1,3-diol can have a cis/trans molar ratio of about 0:1 to about 2:1. Persons of skill in the art will understand that a cis/trans ratio of 0:1 is the equivalent of having the pure trans isomer. In one example, the starting 2,2,4,4-tetramethylcyclobutane-1,3-diol can comprise a substantially pure trans-2,2,4,4-tetramethylcyclobutane-1,3-diol, that is, 2,2,4,4-tetramethylcyclobutane-1,3-diol comprising about 95 mole percent or greater of the trans isomer.

The starting 2,2,4,4-tetramethylcyclobutane-1,3-dione, 3-hydroxy-2,2,4,4-tetramethylcyclobutanone, or 2,2,4,4-tetramethylcyclobutane-1,3-diol is contacted with hydrogen in the presence of a supported ruthenium catalyst. The source and purity of the hydrogen gas are not critical, and the hydrogen gas may comprise fresh hydrogen or a mixture of fresh hydrogen and recycled hydrogen. For example, hydrogen can be a mixture of hydrogen, optionally minor amounts, typically less than about 30 mole %, of components such as CO and $CO_2$, and inert gases, such as argon, nitrogen, or methane. Typically, the hydrogen gas comprises at least about 70 mole % of hydrogen. For example, the hydrogen gas can comprise at least 90 mole % or, in another example, at least 97 mole %, of hydrogen. The hydrogen gas can be obtained from any of the conventional sources well known in the art such as, for example, by partial oxidation or steam reforming of natural gas. Pressure swing absorption can be used if a high purity hydrogen gas is desired. If hydrogen gas recycle is utilized in the isomerization process, then the recycled hydrogen gas may contain minor amounts of one or more products of the isomerization reaction which have not been fully condensed in the product recovery stage downstream from the isomerization reaction.

The temperature and hydrogen pressure used in the isomerization process of the invention can also be varied over a wide range depending on the activity of the catalyst, the mode of operation, and the desired rate of conversion. Typically, the process can be carried out under elevated hydrogen pressures of up to about 50.66 MPa (megapascals) and at temperatures of about 60° C. to about 130° C. or about 65° C. to about 130° C. or about about 70° C. to about 130° C. or about 75° C. to about 130° C. or about about 80° C. to about 130° C. or about 85° C. to about 130° C. or about 90° C. to about 130° C. or about 95° C. to about 130° C. or about 100° C. to about 130° C. or about 60° C. to about 125° C. or about 65° C. to about 125° C. or about about 70° C. to about 125° C. or about 75° C. to about 125° C. or about about 80° C. to about 125° C. or about 85° C. to about 125° C. or about 90° C. to about 125° C. or about 95° C. to about 125° C. or about 100° C. to about 125° C. or about 60° C. to about 120° C. or about 65° C. to about 120° C. or about about 70° C. to about 120° C. or about 75° C. to about 120° C. or about about 80° C. to about 120° C. or about 85° C. to about 120° C. or about 90° C. to about 120° C. or about 95° C. to about 120° C. or about about 100° C. to about 120° C. or about 60° C. to about 115° C. or about 65° C. to about 115° C. or about about 70° C. to about 115° C. or about 75° C. to about 115° C. or about about 80° C. to about 115° C. or about 85° C. to about 115° C. or about 90° C. to about 115° C. or about 95° C. to about 115° C. or about about 100° C. to about 115° C.

In some embodiments of the invention, the reaction conditions can comprise a reaction temperature of about 50 to about 150° C. or 70° C. to about 130° C. or 50° C. to about 130° C. or 70° C. to about 120° C., and a hydrogen pressure of about 0.4 to about 10 megapascals or from 0.4 to about 8.0 megapascals or 0.4 to about 7.0 megapascals or 0.4 to about 7.0 megapascals, or about 0.4 to about 6 megapascals, or about 0.4 to about 5 megapascals, or about 0.4 to about 3.5 megapascals or about 0.4 to or about 2.8 megapascals.

Some additional, more specific ranges of hydrogen pressures are about 0.3 to about 35 MPa, about 0.4 to about 7.0 MPa, 0.3 to about 5.2 MPa, about 0.3 to about 3.5 MPa, and about 0.4 to about 2.8 MPa. Some additional temperature ranges for the isomerization reaction are about 50 to about 120° C. and about 60 to about 110° C. Persons of having ordinary skill in the art will recognize that any combination of the above temperatures and pressures can be used. In one embodiment of the invention, for example, the isomerization process can be carried at a temperature of about 50 to about 120° C. and a hydrogen pressure of about 0.4 to about 2.8 megapascals.

Hydrogenation reaction conditions may include temperatures in the range of 50 to about 120° C. and hydrogen pressures in the range of about 0.4 to about 5 megapascals.

The higher the reaction temperature, the lower the solvent concentration that is needed to provide partial solubility of the monomer during the reaction.

In some embodiments of the invention, the thermodynamic cis/trans ratio of cis-2,2,4,4-tetramethylcyclobutane-1,3-diol produced by the reaction can be greater than the cis/trans 2,2,4,4-tetramethylcyclobutane-1,3-diol solubility ratio in the reaction solvent(s) and wherein the cis-2,2,4,4-tetramethylcyclobutane-1,3-diol isomer concentration can be greater than the cis-2,2,4,4-tetramethylcyclobutane-1,3-diol solubility at reaction temperature.

The definition of thermodynamic cis/trans ratio is known to one of ordinary skill in the art; in some or in all of the embodiments of the invention, thermodynamic cis/trans ratio can be defined as the equilibrium ratio of the cis isomer divided by the trans isomer ratio obtained in solution at the reaction conditions using a particular catalyst and solvent. Thus, in water at 80-100° C. with a ruthenium catalyst the thermodynamic cis/trans ratio is about 2. In alcohols, such as isopropyl alcohol or methyl isobutyl carbinol (MIBC), at 80-100° C. with a ruthenium catalyst the thermodynamic cis/trans ratio is about 1.5.

The definition of cis/trans 2,2,4,4-tetramethylcyclobutane-1,3-diol solubility ratio is also known to one of ordinary skill in the art; in one embodiment, the cis/trans 2,2,4,4-tetramethylcyclobutane-1,3-diol solubility ratio can be defined as the ratio of the cis isomer solubility limit divided by the trans isomer solubility limit at a given temperature for a given solvent or solvents. For example, the cis/trans solubility ratio in water at 80° C. is about 1.0. For MIBC, the cis/trans solubility ratio at 80° C. is about 0.74.

In some embodiments of the invention, the thermodynamic cis/trans 2,2,4,4-tetramethylcyclobutane-1,3-diol ratio produced by the reaction is greater than the cis/trans 2,2,4,4-tetramethylcyclobutane-1,3-diol solubility ratio in the reaction solvent(s) and wherein the cis-2,2,4,4-tetramethylcyclobutane-1,3-diol isomer concentration is greater than the cis-2,2,4,4-tetramethylcyclobutane-1,3-diol solubility at the reaction temperature.

In one embodiment, the catalyst of the present invention comprises ruthenium deposited on a catalyst support. The term "support," as used in the context of the present specification and claims is intended to have its commonly accepted meaning as would be well-understood by persons of ordinary skill in the art, that is, a nominally inert material on which a catalytically active material, e.g., typically a metal, is deposited. The term, "deposited on," as used herein, is understood to mean any known method for adding the metal to the support including, but not limited to, depositing, adsorption, impregnation, ion-exchange, admixing, coprecipitation, and the like. The ruthenium may be deposited on any recognized support material. For example, the support may comprise materials such as chromia, rare earth metal oxides, mixed metal oxides, zinc oxide, alumina, silica, silica-alumina, silicon carbide, zirconia, titania, activated carbon, graphite, graphitized carbon, carbon nano-tubes, zeolites, or mixtures thereof. These support materials are well-known to persons skilled in the art. For example, graphitized carbon supports are described in Rossetti et al. Catalysis Today, 2005, 102-103, pp. 219-224, and in U.S. Pat. No. 7,115,239. The catalyst support may be further compounded with one or more binders to aid in pellet formation. The catalyst support along with any binder can be fabricated in any of the commonly used forms well-known in the art such as, for example, powders, extrudates, chips, granules, monoliths, pellets, cylinders, rings, saddles, spheres, stars, single lobe or multiple-lobe shapes, and the like. Depending on the particular support material employed and/or the method used to prepare a catalyst, ruthenium may be deposited primarily on the surface of the support or distributed throughout the support. In one embodiment, the catalyst comprises ruthenium supported on carbon nanotubes. Carbon nanotubes (also known as fibrils) are well-known in the art as vermicular carbon deposits having diameters less than 1.0 µm. Some additional examples of carbon nanotube diameters are less than 0.5 µm and less than 0.2 µm. Carbon nanotubes can be either multi walled (i.e., have more than one graphene layer more or less parallel to the nanotube axis) or single walled (i.e., have only a single graphene layer parallel to the nanotube axis). Other types of carbon nanotubes are also known, such as fishbone fibrils (e.g., wherein the graphene sheets are disposed in a herringbone pattern with respect to the nanotube axis), etc. As produced, carbon nanotubes may be in the form of discrete nanotubes, aggregates of nanotubes (i.e., dense, microscopic particulate structures comprising entangled carbon nanotubes) or a mixture of both. Some representative examples of carbon nanotubes are described in U.S. Patent Application Publication No.'s 2009 0208391; 2008 0176069; 2008 0175787; 2006 0239893; 2006 0142149; 2006 0142148; and 2003 0039604. The catalyst can have a wide range of ruthenium content. Typically, the total amount of ruthenium present may be about 0.1 to about 10 weight percent based on the total weight of the catalyst. Some additional examples of ruthenium content are about 0.1 to about 9 weight percent, and about 0.2 to about 7 weight percent being more preferred. For example, the catalyst can comprise about 1 to about 9 weight percent ruthenium deposited on a support comprising silica, alumina, silica-alumina, titania, zirconia, activated carbon, graphitized carbon, carbon nanotubes, zeolites, chromia, rare earth metal oxides, or mixtures thereof.

The catalyst may be prepared by conventional techniques such as, for example, vapor deposition or impregnation of ruthenium onto the support material. Ruthenium may be provided as the metal itself or in the form of well-known ruthenium compounds such as, for example, ruthenium salts of inorganic or organic acids, ruthenium oxides, and organometallic complexes containing ruthenium. The support material may be impregnated with ruthenium metal by immersing the support material in a solution of a ruthenium compound in a suitable solvent or by spraying the support material with the solution. The support material typically is dried and the catalyst exposed to a reducing environment, e.g., hydrogen, in order to reduce the ruthenium compounds to ruthenium metal.

The process must be carried out in a solvent that cis-2,2,4,4-tetramethylcyclobutane-1,3-diol is partially soluble at the reaction temperature. The solvent may be selected from a wide variety of compounds or mixture of compounds. The solvent can be any substance that is liquid under the operating conditions of the process, and is substantially inert or shows limited reactivity (e.g., typically less than 1% conversion under process conditions) with respect to the catalyst, hydrogen and 2,2,4,4-tetramethylcyclobutane-1,3-dione, 3-hydroxy-2,2,4,4-tetramethylcyclobutanone, or 2,2,4,4-tetramethylcyclobutane-1,3-diol. Some representative examples of solvents that may be used to partially dissolve the 2,2,4,4-tetramethylcyclobutane-1,3-diol, include water, alcohols, ethers, glycols, glycol ethers, alkanes, esters, and mixtures thereof.

For the purposes of this invention, hydrocarbons comprise alkanes. Alkanes include Isopar™ C Fluid and Isopar™ G Fluid, available from ExxonMobil Chemical Company. Isopar™ C Fluid is a branched alkane consisting primarily of eight carbon hydrocarbons. Isopar™ C Fluid comprises material identified by CAS No. 64742-66-8, also known as naphtha (petroleum) or light alkylates and by CAS No. 90622-56-3 also known as isoalkanes, C7-C10. Isopar™ G Fluid has isoalkanes as the major components. Isopar™ G Fluid and Isopar™ H Fluid comprise materials identified as CAS No. 64742-48-9 also known as hydrotreated heavy naphtha (petroleum). Isopar™ G Fluid also corresponds to EC no. 923-037-2 which is described as C10-C12 isoalkane hydrocarbons with less than 2% aromatics. Isopar™ H Fluid also corresponds to EC No. 918-167-1 which is described as C9-12 isoalkane hydrocarbon with less than 2% aromatics.

Some specific examples of reaction solvents that may be used in the process include, but are not limited to, water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, pentane, hexane, heptane, cyclohexane, octane, decane, dodecane, Isopar™ C, Isopar™ G, Isopar™ H, diethylether, diisopropyl ether, tetrahydrofuran, methyl tert-butyl ether, ethylene glycolmonobutyl ether, diethylene glycol monobutyl ether, ethyl acetate, n-propyl acetate, isopropyl isobutyrate, isobutyl propionate, branched alkanes, isoalkanes, isopropyl alcohol, methyl isobutyl carbinol, octyl acetate, isobutyl isobutyrate, isobutylacetate, methyl butyrate, and mixtures thereof.

In one embodiment, water is a preferred reaction solvent to produce cis-2,2,4,4-tetramethylcyclobutane-1,3-diol. Water can be used with or without a cosolvent. In another embodiment, hydrocarbon(s), such as saturated hydrocarbons, are preferred cosolvents with water because of the limited solubility of 2,2,4,4-tetramethylcyclobutane-1,3-diol in hydrocarbons. Another benefit of using a hydrocarbon as a cosolvent is the solubility of 2,2,4,4-tetramethylcyclobutane-1,3-dione. Thus, 2,2,4,4-tetramethylcyclobutane-1,3-dione can dissolved in the hydrocarbon solvent prior to being added to the reaction vessel. The hydrocarbon cosolvent provides an additional benefit as it aids in mixing the 2,2,4,4-tetramethylcyclobutane-1,3-diol/water system, especially when low ratios of water to 2,2,4,4-tetramethylcyclobutane-1,3-diol are used. A typical hydrocarbon is Isopar™ C. Thus, a typical weight ratio of Isopar™ C:water:starting dione or diol at 100° C. is about 4:1:2. In this case, much of the product cis-2,2,4,4-tetramethylcyclobutane-1,3-diol would exist in the solid phase. Cis/trans ratios greater than about 20 have been achieved with a water and hydrocarbon solvent at 80°-100° C. and in the presence of hydrogen and a ruthenium catalyst.

Solvents containing alcohol functionality are another preferred reaction solvent type of the invention. Secondary and tertiary alcohols are most preferred to primary alcohols due to the reactivity of primary alcohols with ruthenium catalysts. Typical secondary alcohols include 2-propanol, 2-butanol, and 4-methyl-2-pentanol, also known as methyl isobutyl carbinol (MIBC). Hydrocarbons are also the preferred cosolvent for use with these alcohols. Thus, methyl isobutyl carbinol with a hydrocarbon is an example of a preferred solvent system. A typical weight ratio of heptane:methyl isobutyl carbinol:starting dione or diol at 100° C. is about 16:1:4. In this case, much of the product cis-2,2,4,4-tetramethylcyclobutane-1,3-diol would exit in the solid phase. Cis/trans ratios greater than about 15 have been achieved with methyl isobutyl carbinol and heptane solvent at 100° C. and in the presence of hydrogen and a ruthenium catalyst. Another effective mixed solvent system with a secondary alcohol is a hydrocarbon and isopropyl alcohol. Isopar™ G is an example of a hydrocarbon used with isopropyl alcohol. A typical ratio of Isopar™ G:isopropyl alcohol:starting dione or diol is 10:1:4 at 100° C.

Typically, the amount of cis-2,2,4,4-tetramethylcyclobutane-1,3-diol is dissolved in the solvent at a concentration of about 1 to about 60 weight percent at the reaction temperatures, based on the total weight of the tetramethylcyclobutanediol solution. The process operates with partial solubility of cis-2,2,4,4-tetramethylcyclobutane-1,3-diol in the solvent, thus it is instructive to describe the amount of solvent relative to starting 2,2,4,4-tetramethylcyclobutane-1,3-dione or 2,2,4,4-tetramethylcyclobutane-1,3-diol. For example, with a water solvent the typical weight ratio of water to starting 2,2,4,4-tetramethylcyclobutane-1,3-dione or 2,2,4,4-tetramethylcyclobutane-1,3-diol can vary from 0.05 to 3. The lower ratios are preferred at higher temperatures and high ratios are preferred at lower temperatures.

Two preferred reaction solvents systems are used in this invention to produce and recover cis-2,2,4,4-tetramethylcyclobutane-1,3-diol and to recover the catalyst for reuse: one involves use of a solvent comprising a hydrocarbon and water and the other comprising a hydrocarbon and alcohol. Isomerization of trans-2,2,4,4-tetramethylcyclobutane-1,3-diol to the cis isomer is faster in water than in secondary alcohols, so the aqueous system is preferred. Both systems use a hydrocarbon to provide adequate mixing of the heterogeneous reaction mixture. The typical conditions for the hydrocarbon/water system are 100° C., 200-500 psig H2 (1.38-3.45 MPa H2), 4 hours, 5% ruthenium catalyst by wt, hydrocarbon/2,2,4,4-tetramethylcyclobutane-1,3-diol/water: 50/25/8.

In the process of the invention, the catalyst can be washed with a solvent (washing solvent) as step (D) of the process wherein said washing comprises single or multiple washes (in one embodiment, 1 to 5 washes) with at least one polar solvent for washing selected from water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, branched isopropyl alcohol, methyl isobutyl carbinol, isobutyl acetate, methyl butyrate, or mixtures thereof and subsequently either drying the catalyst to remove the polar solvent or 1 to 3 washes with either water or a nonpolar solvent selected from an alkane using a total amount of about 0 to 200 grams polar solvent per gram of catalyst, preferably 30 to 80 grams, polar solvent per gram of catalyst and 0 to 100 grams of either water or nonpolar solvent per gram of catalyst, preferably 5 to 50 grams, of either water or nonpolar solvent per gram of catalyst.

Where the catalyst is washed as in step (D) of the invention, the washing steps can comprise single or multiple washes (in one embodiment, 1 to 5 washes) with a polar solvent selected from water, methanol, or mixtures thereof and then either drying the catalyst, or single or multiple washes (in one embodiment, 1 to 3 washes) with a nonpolar solvent selected from an alkane using a total amount of about 0 to 200 grams polar solvent per gram of catalyst, preferably 30 to 80 grams, and 0 to 100 grams of either water or nonpolar solvent per gram of catalyst, preferably 5 to 50 grams.

Optionally, the solvent used in said Step (D) of the process of the invention can be added to the catalyst and heated at 70° C. to 120° C. for 1 to 4 hours prior to addition of the starting 2,2,4,4-tetramethylcyclobutane-1,3-dione, 3-hydroxy-2,2,4,4-tetramethylcyclobutanone, or 2,2,4,4-tetramethylcyclobutane-1,3-diol, or mixtures thereof.

In the embodiment of the invention where a filtration device is used, the filtration device suitable for the described solid-liquid separations and washes can be batch, semi-continuous or continuous and may be part of the reaction vessel or exist as a separate processing unit. Examples of such filtration devices include but are not limited to pressure filters, vacuum filters, centrifuges, and like devices.

The process may be carried out as a batch, semi-continuous or continuous process, and may utilize a variety of reactor types. In one embodiment of the invention, the process of the invention is carried out as a batch process. Some examples of suitable reactor types include stirred tank, continuous stirred tank, slurry, tubular, fixed bed, and trickle bed. The term "continuous," as used herein, means a process wherein reactants are introduced and products withdrawn simultaneously in an uninterrupted manner. By "continuous" it is meant that the process is substantially or completely continuous in operation in contrast to a "batch" process. The term "batch" process as used herein means a process wherein all the reactants are added to the reactor and then processed according to a predetermined course of reaction during which no material is fed or removed into the reactor. The preferred mode of operation is batch.

An example of the process steps for a batch process can be as listed below.
(1) Charge 2,2,4,4-tetramethylcyclobutane-1,3-dione, 3-hydroxy-2,2,4,4-tetramethylcyclobutanone, and/or 2,2,4,4-tetramethylcyclobutane-1,3-diol, hydrocarbon, water or alcohol, and catalyst. (These can be added in any order. 2,2,4,4-tetramethylcyclobutane-1,3-dione, if used, may be dissolved in the hydrocarbon prior to addition to the reaction vessel);
(2) Purge with N2 and H2. (To remove any air from the reaction vessel.)
(3) Start stirrer. (Any stirrer rate that provides sufficient mixing is acceptable.);
(4) Add H2 to 350 psig (2.41 MPa). (Any hydrogen pressure above about 150 psig (1.03 MPa) is sufficient.);
(5) Heat to 100° C. (Reaction temperatures from 80° C.-110° C., preferably, 50-130.);
(6) Hold 4-5 hours. (The time depends on the amount of feed materials, 2,2,4,4-tetramethylcyclobutane-1,3-dione, 3-hydroxy-2,2,4,4-tetramethylcyclobutanone, and/or 2,2,4,4-tetramethylcyclobutane-1,3-diol, and catalyst used.) The useful time here could be anywhere from 1 hour to 24 hours; more time than that is possible but would not be economically preferred;
(7) Cool (The mixture can be filtered at any temperature greater than 0° C.);
(8) Remove solvent by filtration for recycle (The cis-2,2,4,4-tetramethylcyclobutane-1,3-diol product and catalyst can be washed with hydrocarbon if desired to remove residual solvent).
(9) Add a suitable solvent, such as methanol to dissolve product (cis-2,2,4,4-tetramethylcyclobutane-1,3-diol);
(10) Remove 2,2,4,4-tetramethylcyclobutane-1,3-diol/methanol solution by filtration.
(11) Wash catalyst with methanol. The catalyst is restored to an acceptable activity.
(12) Wash catalyst with hydrocarbon. (To remove residual solvent.)
(13) Add hydrocarbon/water or hydrocarbon/alcohol for next run. Hot water is also effective in restoring catalyst activity. Thus, if lower than desired cis/trans ratios are obtained, simply heating the catalyst with the hydrocarbon/water mixture prior to addition of 2,2,4,4-tetramethylcyclobutane-1,3-diol allows the catalyst to return to acceptable activity.
(14) Add 2,2,4,4-tetramethylcyclobutane-1,3-dione, 3-hydroxy-2,2,4,4-tetramethylcyclobutanone, and/or 2,2,4,4-tetramethylcyclobutane-1,3-diol, and makeup hydrocarbon/water or hydrocarbon/alcohol.
(15) Return to step 4.

The following examples further illustrate how the process of the invention can be carried and utilized, and are intended to be purely exemplary of the invention and are not intended to limit the scope thereof. Unless indicated otherwise, parts are parts by weight, temperature is in degrees C. or is at room temperature, and pressure is at or near atmospheric.

EXAMPLES

The invention is further illustrated by the following examples. All percentages are by weight unless specified otherwise. Analysis of reaction products was performed by gas chromatography using a DB™-Wax column (30 meters×

0.25 mm ID, 0.5 micron film thickness) over a temperature range of 50 to 240° C. and a flame ionization detector. The reaction samples were dissolved in methanol before injection into the gas chromatograph. Trace amounts (e.g., typically less than 0.1 weight percent) of 2,2,4-trimethyl-1,3-pentanediol, 2,4-dimethyl-3-pentanol (diisopropyl carbinol), 2,2,4-trimethyl-3-pentanol, 2,2,4-trimethyl-1-pentanol, 2,2,4-trimethyl-3-oxo-1-pentanol, and 3-hydroxyl-2,2,4,4-cyclobutanone also were detected by GC in the Examples unless indicated otherwise. All pressures are reported as gauge unless indicated otherwise.

Comparative Example 1

Hydrogenation of 2,2,4,4-tetramethylcyclobutane-1,3-dione with 2,2,4,4-tetramethylcyclobutane-1,3-diol soluble in water at 80° C.

A 2 liter Parr autoclave was charged with 50 grams of 2,2,4,4-tetramethylcyclobutane-1,3-dione, 650 grams of dionized water, and 25 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 80° C. with stirring at approximately 1000 rpm (revolutions per minute) and held for 6 hours at 3.5 MPa (500 psig). Analysis of the product by gas chromatography indicated that complete conversion of the 2,2,4,4-tetramethylcyclobutane-1,3-dione was obtained with 100% selectivity to 2,2,4,4-tetramethycyclobutane-1,3-diol with a cis:trans ratio of 2.06:1.

Comparative Example 2

Hydrogenation of 2,2,4,4-tetramethylcyclobutane-1,3-dione with 2,2,4,4-tetramethylcyclobutane-1,3-diol soluble in water at 100° C.

A 2 liter Parr autoclave was charged with 100 grams of 2,2,4,4-tetramethylcyclobutane-1,3-dione, 600 grams of dionized water, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1000 rpm and held for 6 hours at 3.5 MPa (500 psig). Analysis of the product by gas chromatography indicated that 98.5% conversion of the 2,2,4,4-tetramethylcyclobutane-1,3-dione was obtained with 100% selectivity to 2,2,4,4-tetramethycyclobutane-1,3-diol with a cis:trans ratio of 2.15:1.

Comparative Example 3

Hydrogenation of 2,2,4,4-tetramethylcyclobutane-1,3-dione with 2,2,4,4-tetramethylcyclobutane-1,3-diol soluble in isopropyl alcohol at 80° C.

A 2 liter Parr autoclave was charged with 100 grams of 2,2,4,4-tetramethylcyclobutane-1,3-dione, 300 grams of isopropyl alcohol, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 80° C. with stirring at approximately 1400 rpm and held for 6 hours at 3.5 MPa (500 psig). Analysis of the product by gas chromatography indicated that 99.8% conversion of the 2,2,4,4-tetramethylcyclobutane-1,3-dione was obtained with 100% selectivity to 2,2,4,4-tetramethycyclobutane-1,3-diol with a cis:trans ratio of 1.50:1.

Comparative Example 4

Hydrogenation of 2,2,4,4-tetramethylcyclobutane-1,3-dione with 2,2,4,4-tetramethylcyclobutane-1,3-diol soluble in isopropyl alcohol at 100° C.

A 2 liter Parr autoclave was charged with 100 grams of 2,2,4,4-tetramethylcyclobutane-1,3-dione, 300 grams of isopropyl alcohol, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring and held for 6 hours at 3.5 MPa (500 psig). Analysis of the product by gas chromatography indicated that 99.8% conversion of the 2,2,4,4-tetramethylcyclobutane-1,3-dione was obtained with 99.9% selectivity to 2,2,4,4-tetramethycyclobutane-1,3-diol with a cis:trans ratio of 1.54:1.

Comparative Example 5

Hydrogenation of 2,2,4,4-tetramethylcyclobutane-1,3-diol soluble in 4-methyl-2-pentanol at 100° C.

A 2 liter Parr autoclave was charged with 100 grams of 2,2,4,4-tetramethylcyclobutane-1,3-dione, 300 grams of 4-methyl-2-pentanol, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1300 rpm and held for 6 hours at 3.5 MPa (500 psig). Analysis of the product by gas chromatography indicated that complete conversion of the 2,2,4,4-tetramethylcyclobutane-1,3-dione was obtained with 99.5% selectivity to 2,2,4,4-tetramethycyclobutane-1,3-diol with a cis:trans ratio of 1.54:1.

Comparative Example 6

Example Using Water and Isopar™ G with 2,2,4,4-Tetramethylcyclobutane-1,3-Diol Soluble in Water A 300 mL stainless steel autoclave was charged with a mixture of 7.5 g 2,2,4,4-tetramethylcyclobutane-1,3-dione, 60 g water, 60 g n-heptane and a catalyst basket loaded with 5 grams of 2 weight percent Ru on α-alumina catalyst (surface area=10 m2/g, purchased from BASF Catalysts). The autoclave was agitated and purged three times with nitrogen at 0.7 MPa (100 psig) then with hydrogen at 1.4 MPa (200 psig) at ambient temperature. The autoclave was then heated to 120° C. and pressurized to 3.5 MPa (500 psig) with hydrogen. After 180 minutes, the autoclave was cooled and 30 mL of methanol was added. An aliquot of each layer was taken and analyzed by gas chromatography (GC). The non-polar heptane layer contained no detectable byproducts from 2,2,4,4-tetramethylcyclobutane-1,3-dione while, the ratio of cis to trans isomers was 1.81:1 in the aqueous layer. The total 2,2,4,4-tetramethylcyclobutane-1,3-dione conversion was 100%, selectivity was 97.94% and yield was 97.94% with 2,2,4-trimethyl-1,3-pentanediol as the major byproduct at 2.06%.

Comparative Example 7

Example Using Same Amount of Isobutyl Isobutyrate as Isopar™ G (2,2,4,4-tetramethylcyclobutane-1,3-Diol is Soluble) in Example 1

A 2 liter Parr autoclave was charged with 100 grams of 2,2,4,4-tetramethylcyclobutane-1,3-dione, 300 grams isobutyl isobutyrate, 100 grams of dionized water, and 50 grams of 2% ruthenium on alumina catalyst (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 80° C. with stirring at approximately 1400 rpm and held for 6 hours at 3.5 Mpa (500 psig). Analysis of the product by gas chromatography indicated that complete conversion of the 2,2,4,4-tetramethylcyclobutane-1,3-dione was obtained with 99.4% selectivity and a cis:trans 2,2,4,4-tetramethycyclobutane-1,3-diol ratio of 1.55:1.

Comparative Example 8

Example Using Same Amount of Isopropyl Alcohol (2,2,4,4-Tetramethylcyclobutane-1,3-Diol is Soluble) as Water in Example 1

A 2 liter Parr autoclave was charged with 100 grams of 2,2,4,4-tetramethylcyclobutane-1,3-dione, 300 grams Isopar™ G, 100 grams of isopropyl alcohol, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 80° C. with stirring at approximately 1400 rpm and held for 6 hours at 3.5 MPa (500 psig). Analysis of the product by gas chromatography indicated that complete conversion of the 2,2,4,4-tetramethylcyclobutane-1,3-dione was obtained with 100% selectivity to 2,2,4,4-tetramethycyclobutane-1,3-diol with a cis:trans ratio of 1.44:1.

Comparative Example 9

Using Nickel as a Catalyst in Place of Ruthenium

A 300 mL Autoclave Engineers autoclave was charged with 25 grams of 2,2,4,4-tetramethylcyclobutane-1,3-dione, 87.50 grams Isopar™ G, 12.50 grams of water, and approximately 8 grams of washed raney nickel catalyst. The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 5 hours at 3.5 MPa (500 psig). Analysis of the product by gas chromatography indicated that complete conversion of the 2,2,4,4-tetramethylcyclobutane-1,3-dione was obtained with 97.3% selectivity to 2,2,4-tetramethycyclobutane-1,3-diol with a cis:trans ratio of 0.6:1.

Example 1

Hydrogenation/Isomerization at 80° C. with 1:1 Water:Dione and Isopar™ G

A 2 liter Parr autoclave was charged with 100 grams of 2,2,4,4-tetramethylcyclobutane-1,3-dione, 300 grams Isopar™ G, 100 grams of dionized water, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 80° C. with stirring at approximately 1377 rpm and held for 6 hours at 3.5 MPa (500 psig). Analysis of the product by gas chromatography indicated that complete conversion of the 2,2,4,4-tetramethylcyclobutane-1,3-dione was obtained with 100% selectivity to 2,2,4,4-tetramethycyclobutane-1,3-diol with a cis:trans ratio of 21.1:1.

Example 2

Isomerization at 80° C. with 1:1 Water:Diol and Isopar™ G

A 2 liter Parr autoclave was charged with 100 grams of 2,2,4,4-tetramethylcyclobutane-1,3-diol with a cis:trans ratio of 1.10:1, 300 grams Isopar™ G, 100 grams of dionized water, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 80° C. with stirring at approximately 1300 rpm and held for 6 hours at 3.5 MPa (500 psig). Analysis of the product by gas chromatography indicated that the isomerization of the 2,2,4,4-tetramethylcyclobutane-1,3-diol yielded an increase in the cis:trans ratio to 19.6:1.

Example 3

Isomerization at 100° C. with 1:2 Water:Diol and Isopar™ G

A 2 liter Parr autoclave was charged with 100 grams of 2,2,4,4-tetramethylcyclobutane-1,3-diol with a cis:trans ratio of 1.1:1, 350 grams Isopar™ G, 50 grams of dionized water, and 50 grams of 2% ruthenium on alumina (surface area=10 m$^2$/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 21.3:1 with a selectivity of 99.8%

Example 4

Isomerization at 100° C. with 1:2 Water:Diol and Isopar™ G at Smaller Scale (Compared to Example 3)

A 300 mL Parr autoclave was charged with 25 grams of 2 2,4,4-tetramethylcyclobutane-1,3-diol with a cis:trans ratio of 1.1:1, 87.50 grams Isopar™ G, 12.5 grams of dionized water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 20.7:1 with a selectivity of 99.8%.

Example 5

Isomerization at 100° C. with 1:4 Water:Diol and Isopar™ G

A 2 liter Parr autoclave was charged with 100 grams of 2,2 4,4-tetramethylcyclobutane-1,3-diol with a cis:trans ratio of 1.1:1, 375 grams Isopar™ G, 25 grams of dionized water, and 50 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 20.7:1 with a selectivity of 100%.

Example 6

Isomerization at 110° C. with 1:8 Water:Diol and Isopar™ G

A 300 mL Parr autoclave was charged with 25 grams of 2 2,4,4-tetramethylcyclobutane-1,3-diol with a cis:trans ratio of 1.1:1, 96.875 grams Isopar™ G, 3.13 grams of dionized water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 110° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis-trans ratio to 13.1:1 with a selectivity of 100%.

Example 7

Isomerization at 120° C. with 1:10.7 Water:Diol and Isopar™ G

A 300 mL Parr autoclave was charged with 25 grams of 2,2,4,4-tetramethylcyclobutane-1,3-diol with a cis:trans ratio of 1.1:1, 97.66 grams Isopar™ G, 2.34 grams of dionized water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 120° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 5.66:1 with a selectivity of 99.9%.

Example 8

Isomerization at 100° C. with 1:2.33 Water:Diol but No Isopar™ G

A 300 mL Parr autoclave was charged with 70 grams of 2,2,4,4-tetramethylcyclobutane-1,3-diol with a cis:trans ratio of 1.1:1, 30 grams of dionized water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 17.75 hours at 3.5 MPa (500 psig). Analysis of the product by gas chromatography indicated that the isomerization of the 2,2,4,4-tetramethylcyclobutane-1,3-diol yielded an increase in the cis:trans ratio to 14.3:1 with a selectivity of 99.3%.

Example 9

Isomerization at 100° C. with 1:1:2.33 Water:Isopar™ G:Diol

A 300 mL Parr autoclave was charged with 70 grams of 2,2,4,4-tetramethylcyclobutane-1,3-diol with a cis:trans ratio of 1.1:1, 30 grams Isopar™ G, 30 grams of dionized water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 17.75 hours at 3.5 MPa (500 psig). Analysis of the product by gas chromatography indicated that the isomerization of the 2,2,4,4-tetramethylcyclobutane-1,3-diol yielded an increase in the cis:trans ratio to 21.6:1 with a selectivity of 99.5%.

Example 10

Isomerization at 100° C. in Isopropyl Alcohol and Isopar™ G

A 300 mL Parr autoclave was charged with 25 grams of 2,2,4,4-tetramethylcyclobutane-1,3-diol with a cis:trans ratio of 1.1:1, 93.75 grams Isopar™ G, 6.25 grams of isopropyl alcohol, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 5.33:1 with a selectivity of 100%.

Example 11

Isomerization in Isopar™ C and Water

A 300 mL Parr autoclave was charged with 25 grams of 2,2,4,4-tetramethylcyclobutane-1,3-diol with a cis:trans ratio of 1.1:1, 87.50 grams Isopar™ C, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 13.7:1 with a selectivity of 99.9%.

Example 12

Isomerization in n-Heptane and Water

A 300 mL Parr autoclave was charged with 25 grams of 2,2,4,4-tetramethylcyclobutane-1,3-diol with a cis:trans ratio of 1.1:1, 87.50 grams n-heptane, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 15.2:1 with a selectivity of 99.8%.

Example 13

Isomerization in Isopar™ G and Water. (Repeat Conditions in Example 4)

A 300 mL Parr autoclave was charged with 25 grams of 2,2,4,4-tetramethylcyclobutane-1,3-diol with a cis:trans ratio of 1.1:1, 87.5 grams Isopar™ G, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 18.6:1 with a selectivity of 99.8%.

Example 14

Isomerization in Dodecane and Water

A 300 mL Parr autoclave was charged with 25 grams of 2,2,4,4-tetramethylcyclobutane-1,3-diol with a cis:trans ratio of 1.1:1, 87.5 grams dodecane, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 14.9:1 with a selectivity of 99.6%.

Example 15

Isomerization in Pentane and Water

A 300 mL Parr autoclave was charged with 25 grams of 2,2,4,4-tetramethylcyclobutane-1,3-diol with a cis:trans ratio of 1.1:1, 87.5 grams pentane, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 13.2:1 with a selectivity of 99.8%.

Example 16

Isomerization Using Lower Loading of Isopar™ G with Water (Compared to Examples 4 and 13)

A 300 mL Parr autoclave was charged with 25 grams of 2,2,4,4-tetramethylcyclobutane-1,3-diol with a cis:trans ratio of 1.1:1, 40.0 grams Isopar™ G, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 19.2:1 with a selectivity of 99.6%.

Example 17

Isomerization Using Lower Loading of Isopar™ C with Water (Compared to Example 11)

A 300 mL Parr autoclave was charged with 25 grams of 2,2,4,4-tetramethylcyclobutane-1,3-diol with a cis:trans ratio of 1.1:1, 40.0 grams Isopar™ C, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 16.9:1 with a selectivity of 100%.

Example 18

Hydrogenation/Isomerization at 100° C. with 1:2 Water:Dione

A 300 mL Parr autoclave was charged with 25 grams of 2,2,4,4-tetramethylcyclobutane-1,3-dione, 87.50 grams Isopar™ G, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that complete conversion of the 2,2,4,4-tetramethyl-1,3-cyclobutanedione was obtained with 99.9% selectivity to 2,2,4,4-tetramethycyclobutane-1,3-diol with a cis:trans ratio of 17.2:1.

Example 19

Isomerization in Isopar™ G and Water with BASF ESCAT Ru/C

A 300 mL Parr autoclave was charged with 25 grams of 2,2,4,4-tetramethylcyclobutane-1,3-diol with a cis:trans ratio of 1.1:1, 87.50 grams Isopar™ G, 12.50 grams of water, and 5.0 grams of 5% ruthenium on carbon (ESCAT 440 SE13301 powder catalyst, purchased from BASF). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 13.2:1 with a selectivity of 99.9%.

Example 20

Isomerization in Isopar™ G and Water with Aldrich Ru/C

A 300 mL Parr autoclave was charged with 25 grams of 2,2,4,4-tetramethylcyclobutane-1,3-diol with a cis:trans ratio of 1.1:1, 87.50 grams Isopar™ G, 12.50 grams of water, and 5.0 grams of 5% ruthenium on carbon powder (Aldrich catalogue number 20,6180-0). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 23.9:1 with a selectivity of 99.1%.

Example 21

Hydrogenation/Isomerization in IBIB for 17.7 hr

A 300 mL Parr autoclave was charged with 70 grams of 2,2,4,4-tetramethylcyclobutane-1,3-dione, 30 grams isobutyl isobutyrate (IBIB), and 12.5 grams of 2% ruthenium on alumina catalyst (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 17.75 hours at 3.5 Mpa (500 psig). Analysis of the product by gas chromatography indicated that complete conversion of the 2,2,4,4-tetramethylcyclobutane-1,3-dione was obtained with 99.6% selectivity and a cis:trans 2,2,4,4-tetramethycyclobutane-1,3-diol ratio of 7.69:1.

Example 22

Hydrogenation/Isomerization in IBIB for 66 hr

A 300 mL Parr autoclave was charged with 70 grams of 2,2,4,4-tetramethylcyclobutane-1,3-dione, 30 grams isobutyl isobutyrate, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 66 hours at 3.5 Mpa (500 psig). Analysis of the product by gas chromatography indicated that complete conversion of the 2,2,4,4-tetramethylcyclobutane-1,3-dione was obtained with 99.7% selectivity and a cis:trans 2,2,4,4-tetramethycyclobutane-1,3-diol ratio of 9.89:1.

Example 23

Hydrogenation/Isomerization at 100° C. with 1:2 Water:Dione with Catalyst in Screen A 2 liter Parr autoclave was charged with 100 grams of 2,2,4,4-tetramethylcyclobutane-1,3-dione, 375 grams Isopar™ G, 25 grams dionized water, and 50 grams of 2% ruthenium on alumina (surface area=10 m2/g, purchased from BASF Catalysts) placed under a screen in the bottom of the autoclave. The autoclave was pressure purged three times with nitrogen and three times with hydrogen, and the pressure was increased to 3.5 MPa (500 psig) with hydrogen. The autoclave was heated to 100° C. with stirring at approximately 1200 rpm and held for 4 hours at 3.5 MPa (500 psig). Analysis of the product by gas chromatography indicated that complete conversion of the 2,2,4,4-tetramethylcyclobutane-1,3-dione was obtained with 100% selectivity to 2,2,4,4-tetramethycyclobutane-1,3-diol with a cis:trans ratio of 19.8:1.

Example 24

Isomerization at 100° C. with 1:2 Water:Dione with Catalyst in Screen

A 300 mL Parr autoclave was charged with 25 grams of 2,2,4,4-tetramethylcyclobutane-1,3-diol with a cis:trans ratio of 1.1:1, 87.5 grams Isopar™ G, 12.50 grams of water, and 12.5 grams of 2% ruthenium on alumina (surface area=10 m2/g, purchased from BASF Catalysts) placed under a mesh screen in the bottom of the autoclave. The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 15.1:1 with a selectivity of 100%.

Example 25

Isomerization in Isopar™ G and Water Starting with 0.6:1 Cis:Trans Diol

A 300 mL Parr autoclave was charged with 25 grams of 2,2,4,4-tetramethylcyclobutane-1,3-diol with a cis:trans ratio of 0.6:1, 87.50 grams Isopar™ G, 12.50 grams of water, and 5.0 grams of 5% ruthenium on carbon powder (Aldrich catalogue number 20,6180-0). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 21.6:1 with a selectivity of 99.9%.

Example 26

Isomerization in Isopar™ G and Water Starting with Trans Diol

A 300 mL Parr autoclave was charged with 25 grams of 94.3% trans-2,2,4,4-tetramethylcyclobutane-1,3-diol, 87.50 grams Isopar™ G, 12.50 grams of water, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 100° C. with stirring at approximately 1400 rpm and held for 4 hours at 3.5 MPa (500 psig). Analysis of the product by gas chromatography indicated that the isomerization of the 2,2,4,4-tetramethylcyclobutane-1,3-diol yielded an increase in the cis:trans ratio to 9.37:1 with a 100% selectivity.

Example 27

Hydrogenation/Isomerization in Isopar™ G for 16.8 hr

A 300 mL Parr autoclave was charged with 25 grams of 2,2,4,4-tetramethylcyclobutane-1,3-dione, 100 grams Isopar™ G, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 130° C. with stirring at approximately 1400 rpm and held for 16.75 hours at 3.5 MPa (500 psig). Analysis of the product by gas chromatography indicated that complete conversion of the 2,2,4,4-tetramethylcyclobutane-1,3-dione was obtained with 96.1% selectivity to 2,2,4,4-tetramethycyclobutane-1,3-diol with a cis:trans ratio of 4.31:1. The main by-products are 2,2,4-trimethyl-3-pentanol at 1.59%, and 2,2,4-trimethyl-1,3-pentanediol at 2.01%.

Example 28

Hydrogenation/Isomerization in Isopar™ G for 70.8 hr

A 300 mL Parr autoclave was charged with 25 grams of 2,2,4,4-tetramethylcyclobutane-1,3-dione, 100 grams Isopar™ G, and 12.5 grams of 2% ruthenium on alumina (surface area=10 m2/g, purchased from BASF Catalysts). The autoclave was pressure purged three times with nitrogen and three times with hydrogen, and the pressure was increased to 3.5 MPa (500 psig) with hydrogen. The autoclave was heated to 120° C. with stirring at approximately 1400 rpm and held for 70.8 hours at 3.5 MPa (500 psig). Analysis of the product by gas chromatography indicated that complete conversion of the 2,2,4,4-tetramethylcyclobutane-1,3-dione was obtained with 97.4% selectivity to 2,2,4,4-tetramethycyclobutane-1,3-diol with a cis:trans ratio of 8.19:1. The main by-products are 2,2,4-trimethyl-3-pentanol at 1.40%, and 2,2,4-trimethyl-1,3-pentanediol at 0.92%.

Examples 29-56

Recycle experiments using Isopar™ C/water solvent (28 experiments). A series of 28 runs, Examples 29-56, was made using 2,2,4,4-tetramethylcyclobutane-1,3-diol (initial cis/trans ratio; 0.6) or 2,2,4,4-tetramethylcyclobutane-1,3-dione. The results are summarized in Table 1. The general procedure follows.

A 300 mL clean Parr autoclave was charged with Isopar™ C (fresh and recycled), water, 2.5 grams of BASF 5% ruthenium catalyst (for recycle experiments 2.4 g of recovered catalyst from the previous cycle run and 0.1 g fresh 5% ruthenium catalyst) and 25 grams of 2,2,4,4-tetramethylcyclobutane-1,3-diol (cis/trans ratio: 0.6) or 2,2,4,4-tetramethylcyclobutane-1,3-dione (Dione). The autoclave was closed and pressure purged with nitrogen three times and then three times with hydrogen. The autoclave was pressured to approximately 75% of the operating pressure with hydrogen and the stirring initiated. The stir rate was 1420 revolutions per minute. The autoclave was heated to 100° C. when using 2,2,4,4-tetramethylcyclobutane-1,3-diol as a starting material and the pressure adjusted to operating pressure. If 2,2,4,4-tetramethylcyclobutane-1,3-dione was used the temperature would be set 20-25° C. below target to allow for the exothermic reaction, and hydrogen pressure would be adjusted during the first 20 minutes of the experiment while hydrogenation occurred. At the end of the run the temperature was cooled to 40° C. by applying cooling media and the autoclave was vented slowly. The contents of the autoclave were transferred to a filter funnel and vacuum was applied to remove the solvent which was retained for use in the next run. Methanol (150 mL) was used to dissolve 2,2,4,4-tetramethylcyclobutane-1,3-diol crystals remaining on the autoclave equipment and filter pad. The 2,2,4,4-tetramethylcyclobutane-1,3-diol methanol solution was separated from the catalyst by vacuum filtration. Analysis (gc) of the filtrate indicated that the 2,2,4,4-tetramethylcyclobutane-1,3-diol cis/trans ratio had increased with 100% selectivity. Three 50 mL methanol washes were used to wash the catalyst filter cake and a final 50 mL Isopar™ C wash was used to remove the methanol. Vacuum was continued for 2 hours and then the catalyst was transferred to a watch glass for overnight air dry prior to reuse. Catalyst recovery was greater than 2.4 g.

TABLE 1

Recycle experiments in Isopar ™ C/water.

| Cycle | Example | TMCD (g) | Dione (g) | Fresh Isopar ™ C | Recycle Solvent (g) | Water (g) | Temp (° C.) | Pressure (psig)* | Time (h) | Cis/trans |
|---|---|---|---|---|---|---|---|---|---|---|
| 1 | Example 29 | 25 | | 60.00 | 0 | 12.5 | 100 | 500 | 4 | 10.62 |

TABLE 1-continued

Recycle experiments in Isopar™ C/water.

| Cycle | Example | TMCD (g) | Dione (g) | Fresh Isopar™ C | Recycle Solvent (g) | Water (g) | Temp (°C.) | Pressure (psig)* | Time (h) | Cis/trans |
|---|---|---|---|---|---|---|---|---|---|---|
| 2 | Example 30 | 25 | | 60.00 | 0 | 10 | 100 | 500 | 4 | 13.25 |
| 3 | Example 31 | 25 | | 60.00 | 0 | 10 | 100 | 500 | 4 | 11.95 |
| 4 | Example 32 | 25 | | 60.00 | 0 | 10 | 100 | 500 | 4 | 15.03 |
| 5 | Example 33 | 25 | | 60.00 | 0 | 10 | 100 | 500 | 3 | 15.64 |
| 6 | Example 34 | 25 | | 60.00 | 0 | 10 | 100 | 350 | 3 | 15.38 |
| 7 | Example 35 | 25 | | 60.00 | 0 | 10 | 100 | 350 | 2 | 16.16 |
| 8 | Example 36 | 25 | | 60.00 | 0 | 10 | 100 | 350 | 1 | 9.24 |
| 9 | Example 37 | 25 | | 18.13 | 42.04 | 10 | 100 | 350 | 2 | 15.09 |
| 10 | Example 38 | 25 | | 17.03 | 43.00 | 10 | 100 | 350 | 2 | 14.01 |
| 11 | Example 39 | 25 | | 14.75 | 45.26 | 10 | 100 | 350 | 2 | 12.99 |
| 12 | Example 40 | 25 | | 15.30 | 44.72 | 10 | 100 | 350 | 2 | 13.44 |
| 13 | Example 41 | 25 | | 60.06 | 44.41 | 10 | 100 | 350 | 2 | 7.29 |
| 14 | Example 42 | 25 | | 0 | 60.16 | 10 | 100 | 350 | 2 | 11.96 |
| 15 | Example 43 | | 25 | 17.50 | 42.50 | 10 | 100 | 350 | 2 | 5.83 |
| 16 | Example 44 | | 25 | 13.27 | 46.73 | 10 | 100 | 350 | 4 | 11.20 |
| 17 | Example 45 | | 25 | 15.59 | 44.41 | 10 | 100 | 350 | 4 | 10.54 |
| 18 | Example 46 | | 25 | 12.42 | 47.58 | 10 | 100 | 350 | 4 | 11.05 |
| 19 | Example 47 | | 25 | 16.43 | 43.57 | 10 | 100 | 350 | 4 | 12.33 |
| 20 | Example 48 | | 25 | 12.56 | 47.44 | 10 | 100 | 350 | 4 | 8.18 |
| 21 | Example 49 | | 25 | 17.43 | 42.57 | 10 | 100 | 350 | 4 | 8.14 |
| 22 | Example 50 | | 25 | 16.31 | 43.72 | 10 | 100 | 350 | 4 | 4.47 |
| 23 | Example 51 | | 25 | 14.90 | 45.10 | 10 | 100 | 350 | 4 | 3.09 |
| 24 | Example 52 | | 25 | 60.01 | 0 | 10 | 100 | 350 | 4 | 3.26 |
| 25 | Example 53 | 25 | | 50.00 | 0 | 8 | 100 | 500 | 4 | 7.86 |
| 26 | Example 54 | 25 | | 50.00 | 0 | 8 | 100 | 500 | 4 | 7.28 |
| 27 | Example 55 | 25 | | 50.00 | 0 | 8 | 100 | 500 | 4 | 17.28 |
| 28 | Example 56 | 25 | | 50.00 | 0 | 8 | 100 | 500 | 4 | 7.86 |

*(350 psig is 2.41 MPa and 500 psi is 3.45 MPa)
**Dione refers to 2,2,4,4-tetramethylcyclobutane-1,3-dione Examples 57-80

Recycle experiments with n-heptane and methyl isobutyl carbinol (25 experiments). A series of 25 runs, Examples 57-81, was made using 2,2,4,4-tetramethylcyclobutane-1,3-diol (initial cis/trans ratio; 0.6). The results are summarized in Table 2. A typical procedure follows.

Example 71

A 300 mL clean Parr autoclave was charged with n-heptane, MIBC, 3.3 grams of recycled BASF 5% ruthenium catalyst, and 2,2,4,4-tetramethylcyclobutane-1,3-diol. The autoclave was closed and was pressure purged with nitrogen three times and then three times with hydrogen. The autoclave was pressured to approximately 420 psig (2.9 MPa) with hydrogen and the stirring was initiated at 1420 revolutions per minute. The autoclave was heated to 100° C. The pressure was increase to 500 psig (3.45 MPa) with hydrogen. After 5 hours, heating was discontinued and cooling media was applied. When the temperature decreased to 40° C., the autoclave was vented slowly. The contents of the autoclave were transferred to a filter funnel with the aid of approximately 50 ml of n-heptane to recover all the catalyst and crystals. The solvent was removed by vacuum filtration. An additional 200 mL of n-heptane was used in 50-75 mL aliquots to wash the crystals and catalyst in order to remove the MIBC. Vacuum was continued for 20 min to dry the filter cake. Methanol (200 mL) was used to dissolve the 2,2,4,4-tetramethylcyclobutane-1,3-diol crystals and vacuum filtration used to separate the 2,2,4,4-tetramethylcyclobutane-1,3-diol methanol solution from the catalyst. The catalyst was washed three times with 50 ml of methanol and once with 50 ml of n-heptane. The vacuum was continued for 2 hours. The catalyst was transferred to a watch glass to air dry for the next run. 2,2,4,4-tetramethylcyclobutane-1,3-diol was obtained in 100% selectivity in a cis/trans ratio of 14.86.

TABLE 2

Recycle experiments in n-heptane/MIBC at 100° C./500 psig* H2/5 hr.

| Cycle | Run | TMCD (g) | Ruthenium Catalyst (g) | n-Heptane (g) | MIBC (g) | Cis/trans |
|---|---|---|---|---|---|---|
| 1 | Example 57 | 25 | 5.00 | 94 | 6 | 15.35 |
| 2 | Example 58 | 25 | 5.54 | 94 | 6 | 1.14 |
| 3 | Example 59 | 25 | 5.31 | 94 | 6 | 10.90 |
| 4 | Example 60 | 25 | 5.07 | 94 | 6 | 9.86 |
| 5 | Example 61 | 25 | 4.98 | 94 | 6 | 7.38 |
| 6 | Example 62 | 25 | 4.76 | 94 | 6 | 7.95 |
| 7 | Example 63 | 25 | 4.58 | 94 | 6 | 4.15 |
| 8 | Example 64 | 25 | 4.62 | 94 | 6 | 14.31 |
| 9 | Example 65 | 25 | 4.36 | 94 | 6 | 4.92 |
| 10 | Example 66 | 25 | 3.87 | 94 | 6 | 14.17 |
| 11 | Example 67 | 25 | 3.99 | 94 | 6 | 13.73 |
| 12 | Example 68 | 25 | 3.91 | 94 | 6 | 14.30 |
| 13 | Example 69 | 25 | 3.72 | 94 | 6 | 15.26 |
| 14 | Example 70 | 25 | 3.48 | 94 | 6 | 15.71 |
| 15 | Example 71 | 25 | 3.33 | 94 | 6 | 14.86 |
| 16 | Example 72 | 25 | 3.25 | 94 | 6 | 13.87 |
| 17 | Example 73 | 25 | 3.04 | 94 | 6 | 4.67 |
| 18 | Example 74 | 25 | 2.76 | 94 | 6 | 13.00 |
| 19 | Example 75 | 25 | 2.73 | 94 | 6 | 5.79 |
| 20 | Example 76 | 25 | 2.45 | 94 | 6 | 2.40 |
| 21 | Example 77 | 25 | 2.37 | 94 | 6 | 6.15 |
| 22 | Example 78 | 25 | 2.31 | 94 | 6 | 7.63 |
| 23 | Example 79 | 25 | 2.25 + 0.75 fresh | 94 | 6 | 8.16 |
| 24 | Example 80 | 25 | 2.73 | 94 | 6 | 9.36 |
| 25 | Example 81 | 25 | 2.64 | 94 | 6 | 9.26 |

*500 psi is 3.45 MPa

The invention has been described in detail with reference to the embodiments disclosed herein, but it will be understood that variations and modifications can be effected within the spirit and scope of the invention.

We claim:

1. A process for the preparation of cis-2,2,4,4-tetramethylcyclobutane-1,3-diol, the process comprising:
contacting a monomer selected from 2,2,4,4-tetramethylcyclobutane-1,3-dione, 3-hydroxy-2,2,4,4-tetramethylcyclobutanone, 2,2,4,4-tetramethylcyclobutane-1,3-diol having a starting cis:trans molar ratio of 0:1 to about 2:1, or mixtures thereof with hydrogen in the presence of a reaction solvent in which the resulting cis-2,2,4,4-tetramethylcyclobutane-1,3-diol is partially soluble, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-dial having a final cis:trans molar ratio of from 2:1 to about 25:1,
wherein the thermodynamic cis/trans 2,2,4,4-tetramethylcyclobutane-1,3-diol ratio produced by the reaction is greater than the cis/trans 2,2,4,4-tetramethylcyclobutane-1,3-diol solubility ratio in the reaction solvent, and wherein the cis-2,2,4,4-tetramethylcyclobutane-1,3-diol isomer concentration in the reaction solvent is greater than the cis-2,2,4,4-tetramethylcyclobutane-1,3-diol solubility at the reaction temperature.

2. The process according to claim 1 wherein said reaction conditions comprise a reaction temperature of about 50 to about 150° C. and a hydrogen pressure of about 0.4 to about 10 megapascals.

3. The process according to claim 1 wherein said reaction conditions comprise a reaction temperature of about 70 to about 130° C. and a hydrogen pressure of about 0.4 to about 5.0 megapascals.

4. The process according to claim 1 or 2 wherein the catalyst comprises about 1 to about 9 weight percent ruthenium and the support comprises activated carbon, carbon nanotubes, graphitized carbon, silica, alumina, titania, zirconia, or a mixture thereof.

5. The process according to claims 1 or 2 wherein said catalyst further comprises a metal selected from nickel, copper, cobalt, rhenium, platinum, palladium, rhodium, gold, silver, chromium, manganese, tin, or mixtures thereof.

6. The process according to claim 1 wherein said reaction solvent is selected from water, alcohols, ethers, glycols, glycol ethers, alkanes, esters, or mixtures thereof.

7. The process according to claim 6 wherein the reaction solvent is selected from water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, branched alkanes, isoalkanes, isopropyl alcohol, methyl isobutyl carbinol, isobutyl acetate, methyl butyrate, or mixtures thereof.

8. The process of claim 6 wherein said reaction solvent is selected from at least one alkane, water, or mixtures thereof.

9. The process of claim 8 wherein said reaction solvent is selected from at least one alkane or a mixture of water and at least one alkane.

10. The process of claim 9 wherein said alkane is an isoalkane, a branched alkane, or a cyclic alkane.

11. The process of claim 10 wherein said branched alkane comprises from 6 to 18 carbon atoms.

12. The process of claim 8 wherein said reaction solvent is water.

13. The process of claim 8 wherein said reaction solvent is a mixture of water and at least one alkane.

14. The process according to claim 1 which is conducted in the liquid phase.

15. A process for the preparation of cis-2,2,4,4-tetramethylcyclobutane-1,3-diol, the process comprising:
contacting a monomer selected from 2,2,4,4-tetramethylcyclobutane-1,3-dione, 3-hydroxy-2,2,4,4-tetramethylcyclobutanone, and 2,2,4,4-tetramethylcyclobutane-1,3-diol having a starting cis:trans molar ratio of 0:1 to about 2:1, or mixtures thereof with hydrogen in the presence of a reaction solvent comprising water, at least one hydrocarbon, or mixtures thereof, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from 2:1 to about 25:1,
wherein the thermodynamic cis/trans 2,2,4,4-tetramethylcyclobutane-1,3-diol ratio produced by the reaction is greater than the cis/trans 2,2,4,4-tetramethylcyclobutane-1,3-diol solubility ratio in the reaction solvent(s), and wherein the cis-2,2,4,4-tetramethylcyclobutane-1,3-diol isomer concentration in the reaction solvent is greater than the cis-2,2,4,4-tetramethylcyclobutane-1,3-diol solubility at the reaction temperature.

16. A process for the preparation of cis-2,2,4,4-tetramethylcyclobutane-1,3-diol, the process comprising:

contacting a monomer selected from 2,2,4,4-tetramethylcyclobutane-1,3-dione, 3-hydroxy-2,2,4,4-tetramethylcyclobutanone, 2,2,4,4-tetramethylcyclobutane-1,3-diol having a starting cis:trans molar ratio of 0:1 to about 2:1, or mixtures thereof with hydrogen in the presence of a reaction solvent comprising at least one hydrocarbon, at least one secondary alcohol, or mixtures thereof, and further in the presence of a catalyst comprising about 0.1 to about 10 weight percent ruthenium, based on the total weight of the catalyst, deposited on a support material, under reaction conditions sufficient to produce a 2,2,4,4-tetramethylcyclobutane-1,3-diol having a final cis:trans molar ratio of from 2:1 to about 25:1, wherein the thermodynamic cis/trans 2,2,4,4-tetramethylcyclobutane-1,3-diol ratio produced by the reaction is greater than the cis/trans 2,2,4,4-tetramethylcyclobutane-1,3-diol solubility ratio in the reaction solvent(s), and wherein the cis-2,2,4,4-tetramethylcyclobutane-1,3-diol isomer concentration in the reaction solvent is greater than the cis-2,2,4,4-tetramethylcyclobutane-1,3-diol solubility at the reaction temperature.

* * * * *